US009290442B2

(12) United States Patent
Unkefer et al.

(10) Patent No.: US 9,290,442 B2
(45) Date of Patent: *Mar. 22, 2016

(54) PREPARATION OF 4-AMINO-2,4-DIOXOBUTANOIC ACID

(71) Applicants: Los Alamos National Security, LLC, Los Alamos, NM (US); New Mexico Highlands University, Las Vegas, NM (US)

(72) Inventors: Pat J. Unkefer, Los Alamos, NM (US); Rodolfo A. Martinez, Sante Fe, NM (US); David R. Glass, Las Vegas, NM (US)

(73) Assignees: Los Alamos National Security, LLC, Los Alamos, NM (US); New Mexico Highlands University, Las Vegas, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,423

(22) Filed: Sep. 15, 2014

(65) Prior Publication Data

US 2015/0065750 A1    Mar. 5, 2015

Related U.S. Application Data

(63) Continuation-in-part of application No. 13/828,905, filed on Mar. 14, 2013, now Pat. No. 9,045,392.

(60) Provisional application No. 62/040,376, filed on Aug. 21, 2014.

(51) Int. Cl.
*C07C 229/00* (2006.01)
*C07C 231/06* (2006.01)
*C07C 253/30* (2006.01)

(52) U.S. Cl.
CPC ............ *C07C 231/065* (2013.01); *C07C 253/30* (2013.01)

(58) Field of Classification Search
CPC   C07C 231/065; C07C 253/30; C07C 235/80; C07C 255/23
See application file for complete search history.

(56) References Cited

U.S. PATENT DOCUMENTS

| 3,899,585 | A | 8/1975 | Misato et al. |
| 4,336,397 | A | 6/1982 | Cragoe, Jr. et al. |
| 5,922,649 | A | 7/1999 | Pehu et al. |
| 6,083,876 | A | 7/2000 | Jokinen et al. |
| 6,288,240 | B1 | 9/2001 | Martinez et al. |
| 6,329,571 | B1 | 12/2001 | Hiei |
| 6,448,202 | B1 | 9/2002 | Miyazawa et al. |
| 6,555,500 | B1 | 4/2003 | Unkefer et al. |
| 6,593,275 | B1 | 7/2003 | Unkefer et al. |
| 6,703,346 | B2 | 3/2004 | Herold et al. |
| 6,767,865 | B2 | 7/2004 | Den Tandt et al. |
| 6,803,345 | B2 | 10/2004 | Herold et al. |
| 6,831,040 | B1 | 12/2004 | Unkefer et al. |
| 6,906,004 | B2 | 6/2005 | Parrish et al. |
| 7,001,869 | B2 | 2/2006 | Johnson |
| 7,094,735 | B2 | 8/2006 | Herold et al. |
| 7,776,790 | B2 | 8/2010 | Herold et al. |
| 8,551,917 | B2 | 10/2013 | Unkefer et al. |
| 8,759,256 | B2 | 6/2014 | Parrish et al. |
| 8,802,595 | B2 | 8/2014 | Unkefer et al. |
| 9,045,392 | B2 * | 6/2015 | Unkefer ............... C07C 253/30 |
| 2003/0032149 | A1 | 2/2003 | Lalonde |
| 2003/0144147 | A1 | 7/2003 | Herold et al. |
| 2003/0148889 | A1 | 8/2003 | Herold et al. |
| 2003/0153461 | A1 | 8/2003 | Parrish et al. |
| 2003/0153462 | A1 | 8/2003 | Herold et al. |
| 2004/0063582 | A1 | 4/2004 | Johnson |
| 2004/0127364 | A1 | 7/2004 | Herold et al. |
| 2004/0132621 | A1 | 7/2004 | Frisch et al. |
| 2004/0132624 | A1 | 7/2004 | Frisch et al. |
| 2004/0209777 | A1 | 10/2004 | Gemma et al. |
| 2005/0137091 | A1 | 6/2005 | Herold et al. |
| 2005/0170967 | A1 | 8/2005 | Parrish et al. |
| 2005/0232868 | A1 | 10/2005 | Rennie et al. |
| 2006/0090219 | A1 | 4/2006 | Kisaka |
| 2006/0205601 | A1 | 9/2006 | Herold et al. |

(Continued)

FOREIGN PATENT DOCUMENTS

| EP | 10955565 A1 | 5/2001 |
| EP | 1647181 | 4/2006 |

(Continued)

OTHER PUBLICATIONS

International Patent Application No. PCT/US2014/050274, International Search Report dated Nov. 18, 2014.

(Continued)

*Primary Examiner* — Yevegeny Valenrod
*Assistant Examiner* — Blaine G Doletski
(74) *Attorney, Agent, or Firm* — Mark D. Miller; William K. Nelson

(57) ABSTRACT

A process for synthesizing 4-amino-2,4-dioxobutanoic acid involves reacting diethyl oxalate with an alkoxide in ethanol to form a reaction mixture, and afterward adding ethyl cyanoacetate to the reaction mixture and allowing a reaction to proceed under conditions suitable to form a first reaction product of the formula diethyl 2-cyano-3-hydroxy-butenedioate, and then isolating the diethyl 2-cyano-3-hydroxy-butenedioate, and afterward reacting the diethyl-2-cyano-3-hydroxy-butenedioate with an aqueous hydroxide under conditions suitable to form 4-amino-2,4-dioxobutanoic acid.

10 Claims, 4 Drawing Sheets

(56) References Cited

U.S. PATENT DOCUMENTS

| | | |
|---|---|---|
| 2007/0105719 A1 | 5/2007 | Unkefer et al. |
| 2010/0184599 A1 | 7/2010 | Parrish et al. |
| 2012/0090365 A1 | 4/2012 | Ersek et al. |
| 2014/0038824 A1 | 2/2014 | Unkefer et al. |
| 2014/0275624 A1 | 9/2014 | Unkefer et al. |
| 2015/0065751 A1* | 3/2015 | Unkefer .............. C07C 231/065 562/568 |

FOREIGN PATENT DOCUMENTS

| | | |
|---|---|---|
| JP | s4629767 | 8/1971 |
| JP | H1059808 | 3/1998 |
| JP | 2005512963 | 5/2005 |
| RU | 2277323 | 6/2006 |
| RU | 2333245 | 9/2008 |
| WO | 0154500 | 8/2001 |
| WO | 03026422 | 4/2003 |
| WO | 03026429 | 4/2003 |
| WO | 2004054360 | 7/2004 |
| WO | 2007056409 | 5/2007 |

OTHER PUBLICATIONS

International Patent Application No. PCT/US2014/050274, Written Opinion of the International Search Authority dated Nov. 18, 2014.
Weygand, F., et al., Synthese von 1.5-Diaza-cyclooctan-dion-(4.8)-dicarbosaure-(2.6). Chemische Berichte, 1954, 87(4): 482-488—with English Abstract.
International Search Report from PCT/US14/21620 dated Jun. 10, 2014 (citing U.S. Pat. No. 4,336,397, Verbic, T. et al. and Tomassini, J. et al.).
Verbic, T. et al., An LFER study of the protolytic equilibria of 4-aryl-2,4-dioxobutanoic acids in aqueous solutions. Journal of the Serbian Chemical Society, Jan. 2007, 72(12):1201-1216. (cited in the International Search Report from PCT/US14/21620 dated Jun. 10, 2014).
Tomassini, J. et al., Inhibition of cap (m7GpppXm)—dependent endonuclease of influenza virus by 4-substituted 2,4-dioxobutanoic acid compounds. Antimicrob Agents Chemother, Dec. 1994, 38(12):2827-37. (cited in the International Search Report from PCT/US14/21620 dated Jun. 10, 2014).
Meister, A., Preparation and Enzymatic Reactions of the Keto Analogues of Asparagine and Glutamine. J. Biol. Chem., 1953, 200:571-589.
Weygand, F., et al., Synthese von 1.5-Diaza-cyclooctan-dion-(4.8)-dicarbosaure-(2.6). Chemische Berichte, 1954, 87(4): 482-488.
Stephani, R.A., Meister, A., Structure of the Dimeric alpha-Keto Acid Analogue of Asparagine. The Jounrnal of Biological Chemistry, Dec. 1971, 246(23):7115-7118.
Ta, T.C., Joy, K.W., and Ireland, R.J., Utilization of the Amide Groups of Asparagine and 2-Hydroxysuccinamic Acid by Young Pea Leaves. Plant Physiology, 1984, 75: 527-530.
Tadashi, A. et al., Herbicidal Composition Containing Pyroglutamic Acid or its Salt, English Abstract of Japanese Patent Publication JPH1059808, Mar. 3, 1998. Machine-generated English translation.
English Machine Translation of Japanese Patent Application Publication JP10059808 published on Mar. 3, 1998, the English Machine Translation was accessed and downloaded as early as Apr. 1, 2014.
Brochure: Take Off, Verdesian Life Sciences, LLC, 12 Pages, Aug. 2013.
Nanjo, T. et al., "Biological functions of proline in morphogenesis and osmotolerance revealed in antisense transgenic Arapidopsis thanliana." The Plant Journal, vol. 18, No. 2 (Feb. 1999) pp. 185-193.
Walkey et al., "The inactivation of virus in cultured shoot tips of Nicotiana rustica L." J. Gen. Virol., 1969, 5, 237-241.
English Abstract of Japanese Patent Publication JP2005512963, published May 12, 2005. The English abstract was accessed and downloaded from European Patent Organization, http://www.epo.org/searching/free/espacenet.html on Aug. 20, 2014.
English Abstract of WIPO Patent Publication WO2007056409 published on May 18, 2007. The English abstract was accessed and downloaded from European Patent Organization, http://www.epo.org/searching/free/espacenet.html on Oct. 17, 2014.
English Abstract of Russian Patent Publication RU2277323 published on May 10, 2006. The English abstract was accessed and downloaded from http://bd.patent.su/2277000-2277999/pat/servl/servlet4b05.html on Oct. 17, 2014.
Method of Constructing Plant Showing Improved Growth Under Regulation of Nitrogen, English Abstract of Russian Patent Publication RU2333245, Sep. 10, 2008, European Patent Organization, http://www.epo.org/searching/free/espacenet.html.
English Abstract of Russian Patent Publication RU2006104849 published on Jun. 27, 2006. (Issued as RU2333245) The English abstract was accessed and downloaded from European Patent Organization, http://www.epo.org/searching/free/espacenet.html on Oct. 17, 2014.
Frisch, G. et al., Microemulsion Concentrates, English Abstract of WIPO Patent Publication WO2004054360, Jul. 1, 2004, European Patent Organization, http://www.epo.org/searching/free/espacenet.html.
International Search Report from WO03026429 dated May 12, 2002.
Rooney et al., "Inhibitors of Glycolic Acid Oxidase. 4-Substituted 3-Hydroxy-1H-pyrrole-2,5-dione derivatives," J. Med. Chem., 1983, vol. 26, pp. 700-714.
Williams et al., "Inhibitors of Glycolic Acid Oxidase. 4-Substituted 2,4-Dioxobutanoic Acid Derivatives," J. Med. Chem., 1983, vol. 26, pp. 1196-1200.

* cited by examiner tion Ser. No. 13/828,905 filed on Mar. 14, 2013, and this

PREPARATION OF 4-AMINO-2,4-DIOXOBUTANOIC ACID

PRIORITY

This application is a continuation-in-part of U.S. application Ser. No. 13/828,905 filed on Mar. 14, 2013, and this application also claims the benefit of U.S. provisional application Ser. No. 62/040,376 filed on Aug. 21, 2014, both of which are incorporated herein by this reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to the preparation of 4-amino-2,4-dioxobutanoic acid.

BACKGROUND OF THE INVENTION

The compound 4-amino-2,4-dioxobutanoic acid is a metabolite found in plants (see, for example: Ta et al., "Utilization of the Amide Groups of Asparagine and 2-Hydroxysuccinamic Acid by Young Pea Leaves," Plant Physiology, July 1984, vol. 75, pp. 527-530, incorporated by reference). Meister reported in "Preparation and Enzymatic Reactions of the Keto Analogues of Asparagine and Glutamine," J. Biol. Chem., vol. 200, (1953), pp. 571-589, which is incorporated by references, a process for synthesizing 4-amino-2,4-dioxobutanoic acid. This preparation was on a small scale and was expensive because it required crude rattlesnake venom.

SUMMARY OF THE INVENTION

The present invention provides a process for synthesizing 4-amino-2,4-dioxobutanoic acid that involves reacting diethyl oxalate with a suitable alkoxide (such as, without limitation, sodium, potassium, lithium, cesium, calcium) in a suitable solvent to form a reaction mixture, and afterward adding ethyl cyanoacetate to the reaction mixture and allowing a reaction to proceed under conditions suitable to form a first reaction product of the formula diethyl 2-cyano-3-hydroxy-butenedioate, and isolating said first reaction product of diethyl 2-cyano-3-hydroxy-butenedioate, and then reacting said first reaction product of diethyl 2-cyano-3-hydroxy-butenedioate with a suitable aqueous hydroxide (such as, without limitation, sodium, potassium, lithium, cesium, calcium) under conditions suitable to form 4-amino-2,4-dioxobutanoic acid.

In an embodiment, a process for synthesizing 4-amino-2,4-dioxobutanoic acid includes the steps of reacting diethyl oxalate with an alkoxide (such as, without limitation, sodium, potassium, lithium, cesium, calcium) in an alcoholic solvent to form a reaction mixture, then adding ethyl cyanoacetate to the reaction mixture. After allowing the ingredients to react, the reaction mixture was extracted using dichloromethane and water. The aqueous layer was separated from the dichloromethane layer, acidified, and extracted with additional dichloromethane. In some embodiments, the dichloromethane layers may then be combined; however in this case they were not. Removal of the dichloromethane left diethyl 2-cyano-3-hydroxy-butenedioate. The diethyl 2-cyano-3-hydroxy-butenedioate was combined with an aqueous hydroxide (such as, without limitation, sodium, potassium, lithium, cesium, calcium) to form a reaction mixture that was subjected to conditions suitable for forming 4-amino-2,4-dioxobutanoic acid.

DETAILED DESCRIPTION

This invention is concerned with the synthesis of 4-amino-2,4-dioxobutanoic acid and derivatives thereof. An exemplary reaction sequence begins by reacting sodium metal with ethanol to form sodium ethoxide, then adding diethyl oxalate to the sodium ethoxide, and then slowly adding ethyl cyanoacetate. It is to be appreciated that potassium, lithium, cesium, calcium or other metals may alternatively be used instead of sodium to form the ethoxide. An acidic workup resulted in diethyl 2-cyano-3-hydroxy-butenedioate which was isolated as a pale yellowish solid. Without further purification, the diethyl 2-cyano-3-hydroxy-butenedioate was heated in the presence of aqueous sodium hydroxide. It is to be appreciated that potassium, lithium, cesium, calcium or other metals may alternatively be used instead of sodium as the hydroxide. The chemical reactions summarized below.

Figure 1:
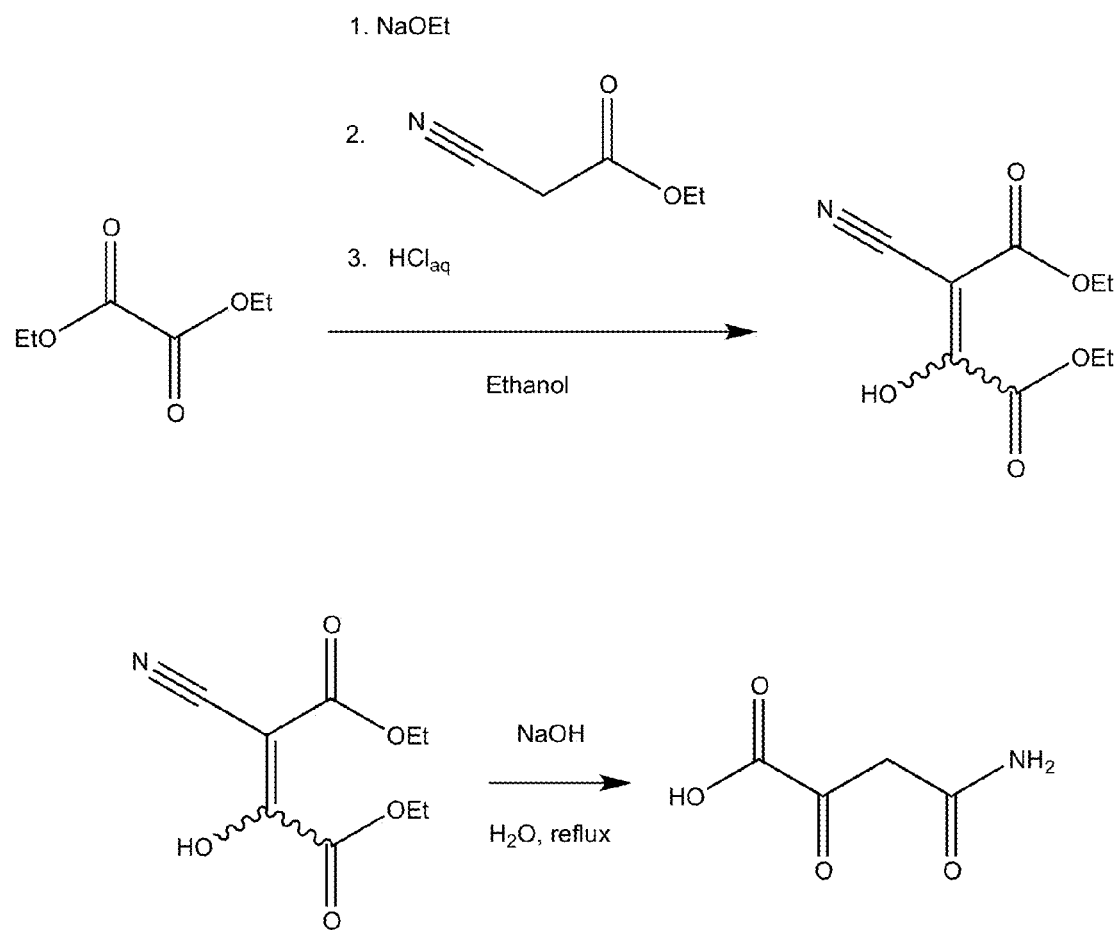
FIG. 1 is a typical reaction scheme for synthesis of 4-amino-2,4-dioxobutanoic acid.
Figure 2:
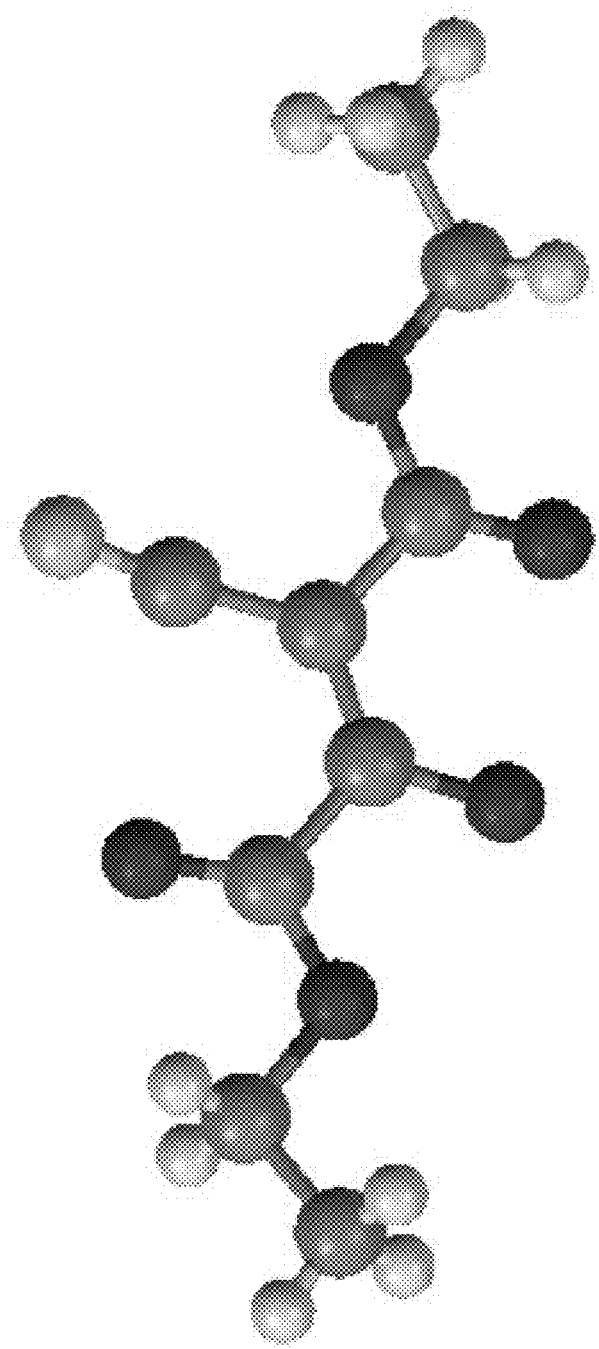
FIG. 2 is an x-ray crystal structure of diethyl 2-cyano-3-hydroxy-butenedioate.

The details of a typical diester synthesis now follow. An exemplary synthesis of diethyl 2-cyano-3-hydroxy-butenedioate began by fitting a dry 5-liter Morton flask with a reflux condenser. Absolute ethanol (1040 milliliters) was added to the flask under nitrogen, and sodium metal (35.2 g, 1.53 moles, 1.0 equivalent) was placed into the absolute ethanol also under nitrogen while an ice-water bath was used to cool the flask. After the mixture was stirred for about 6 hours, the ice water bath was removed and the reaction was brought to room temperature. The temperature rose briefly to about 30° C. After about 24 hours, the sodium metal had completely dissolved. Diethyl oxalate (219.2 grams, 1.5 moles, 1.0 equivalent) was added neat in a single portion to the flask. While the reaction mixture was stirring, a solution of ethyl cyanoacetate (169.7 grams, 1.5 moles, 1.0 equivalent) in absolute ethanol (1000 milliliters) was added dropwise at room temperature to the reaction mixture. The addition, which was made at a rate of 1 drop every 2 to 3 seconds, took about 2½ days to complete. Afterward, the reaction mixture was extracted with dichloromethane (1000 milliliters) and deionized water (1000 milliliters). The aqueous layer was extracted with an additional 100 milliliters dichloromethane. The resulting aqueous layer had a pH of about 8-9. The layers were separated. The aqueous layer was acidified to a pH of about 1 with 6 M HCl. The acidic aqueous layer was then extracted with dichloromethane (1000 milliliters) and the layers were separated. The organic layer was evaporated by rotary evaporator to yield diethyl 2-cyano-3-hydroxy-butenedioate as a pale yellowish solid (304 grams, 95%) that was used without any further purification.

The 4-amino-2,4-dioxobutanoic acid was synthesized using the diethyl-2-cyano-3-hydroxy-butenedioate prepared as described above. A 5-liter Morton flask was equipped with an air condenser. Diethyl-2-cyano3-hydroxy-butenedioate (214.2.grams, 1.00 mole, 1.0 equivalent) was dissolved in aqueous sodium hydroxide (1.0 M, 1000 milliliters, 4.0 equivalents) at room temperature in the flask while stirring the contents of the flask. After about one minute, a heating mantle was placed underneath the flask. Using the heating mantle, the flask was heated sufficiently for reflux while the reaction mixture was stirred. After about 4½ hours at reflux, the heat was removed and the reaction mixture was allowed to cool to room temperature and was stirred overnight at room temperature. The reaction solution was placed into an ice-water bath and acidified using 6M HCl until the pH of was equal to about 1. Solids formed after about 5 minutes. The solids were filtered. The colorless solids (27 grams) were analyzed by NMR and were found to include carbonate (13C-NMR δ=162 ppm). The bulk of the water was evaporated using a rotary evaporator at about 40° C. The solids were stirred in acetone (1000 milliliters) and then filtered. The acetone was then removed under a vacuum using a rotary evaporator followed by a vacuum pump to yield the 4-amino-2,4-dioxobutanoic acid in 56% yield (74 grams) as a light yellow solid that was used without further purification.

The details of another exemplary synthesis now follow. In a dry 3-L round bottom flask fitted with a reflux condenser, sodium metal (21.5 g, 0.935 mol, 1.0 eq) was placed into absolute ethanol (690 mL) under argon, in a room temperature water bath for 24 hours while stirring. The temperature did not rise from ambient. After 24 hours, the sodium metal had completely reacted to form sodium ethoxide. Diethyl oxalate (136.5 g, 0.935 mol, 1.0 eq) was added neat in a single portion, and then ethyl cyanoacetate (105.7 g, 0.935 mol, 1.0 eq) as a solution in absolute ethanol (500 mL) was added dropwise at room temperature while stirring. This addition was made at a rate of 1 drop every 2-3 seconds, and took about 1½ days to complete. The volatiles were evaporated by rotary evaporator to yield the diethyl 2-cyano-3-hydroxy-butenedioate sodium salt as a pale yellowish sticky solid and residual ethanol. This material was used without further purification in the subsequent step (239 g, quantitative, 92.3% pure by mass).

In a 1-L round bottom flask, diethyl 2-cyano-3-hydroxy-butenedioate sodium salt (11.2 g, 0.0475 mol, 1.0 eq) was dissolved in aqueous sodium hydroxide (1M, 95 mL, 0.095 mol, 2.0 eq) at room temperature. After one minute, the diethyl 2-cyano-3-hydroxy-butenedioate sodium salt was completely dissolved and the flask was placed into a preheated heating mantle. The solution was heated at reflux with stirring for 4½ hours. The homogeneous solution was then removed from heat and stirred at room temperature overnight. The homogeneous solution was then placed into an ice-water bath and acidified to pH=3 using 6M HCl (10 mL). It is important to note here that pH 4 will not hydrolyze the cyano group, and pH lower than 3 risks hydrolyzing the amide. The reaction bubbled, which indicated the liberation of $CO_2$. An aliquot was examined by $^{13}$C-NMR, and showed that the cyano group had been hydrolyzed to the amide and that the reaction had decarboxylated. This was ascertained by the disappearance of the signal at ~120 ppm and appearance of a new peak at ~172. The reaction was then treated with 6M sodium hydroxide (13 mL) to adjust the pH to 14. The reaction was stirred at room temperature for approximately 5 days. As the solution stirred, it became heterogeneous. At this time the solution was yellow. An aliquot was evaporated to show that the ester (NMR peaks at 62 and 13 ppm) had been 90% hydrolyzed. The reaction was then filtered to remove 3.8 grams colorless solid that did not comprise the desired product. After this filtration was performed, the homogeneous solution was placed into a room-temperature water bath. The reaction was then acidified to pH=4.5 using 1M HCl (20 mL) The reaction volume was reduced by 75 mL using a rotary evaporator (from its initial volume of 105 mL). At this time, solids began to precipitate and the reaction was left to sit overnight at room temperature (pH=4-5). The reaction was filtered, removing 1.4 grams colorless solid that did not comprise the desired product. The volume was reduced by half on the rotary evaporator, and 2-propanol (2 mL) was added. Solids formed immediately. The solids were removed by filtration to yield 1.4 grams of colorless solid that did not comprise the desired product. The remaining solution was evaporated by rotary evaporator followed by high-vacuum pump to yield a yellow solid (5.0 g, 81%). $^{13}$C-NMR ($D_2O$, 75 MHz): δ=176.1, 175.2, 174.2, 44.9.

Figure 3:
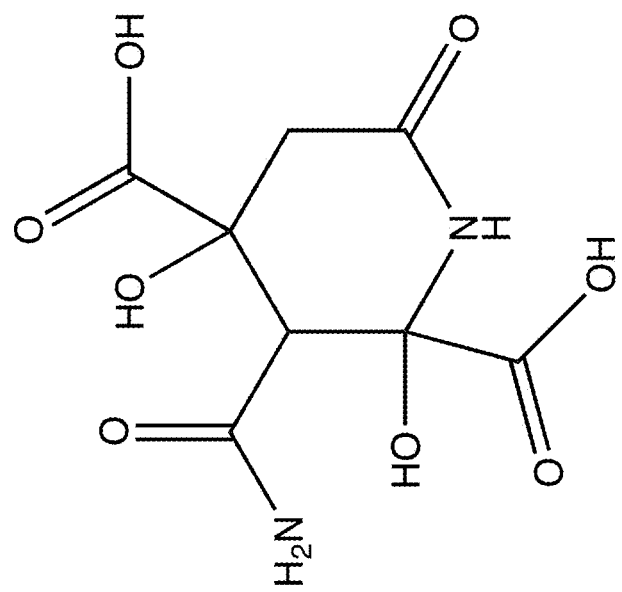
FIG. 3 shows different forms of 4-amino-2,4-dioxobutanoic acid that may be made by the synthesis of the present invention.
Figure 3:
Figure 3:
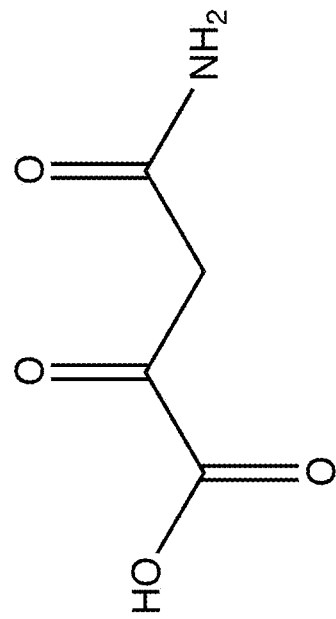
Figure 4:
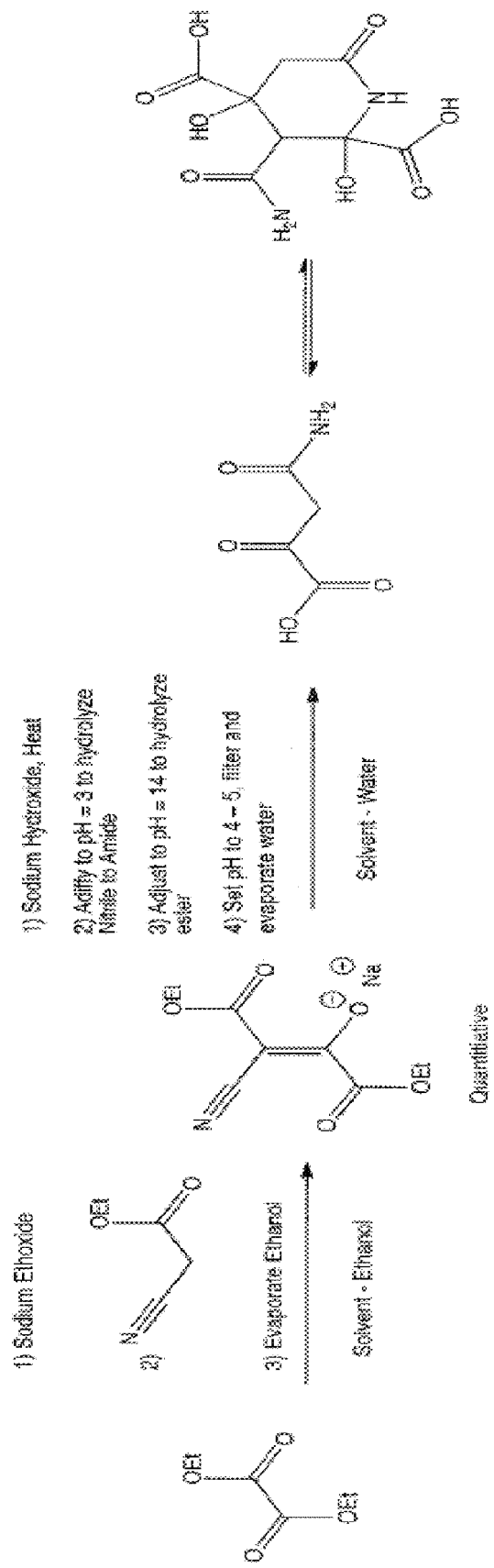
FIG. 4 is a diagram of an embodiment of an overall process of the present invention.

NMR indicates that the monomer and dimeric forms of the compound are in equilibrium as shown in FIG. 3.

The 4-amino-2,4-dioxobutanoic acid may be used as a foliar spray on the leaves on agricultural crops. Plants would respond to treatments of such a spray by increasing their tillers. On cereal plants (for example, wheat, rice, barley), these are the structures on which the grain heads form and are developed. Thus, the greater number of tillers, the greater the number of seed heads, which translates into greater grain yield. Soybeans would respond to 4-amino-2,4-dioxobutanoic acid by increasing their root nodules, the site of biological reduction of $N_2$ gas from the atmosphere to ammonia which the plants can use as a nitrogen source. This means that less expensive nitrogen-containing fertilizer would be needed by the farmer.

Although the present invention has been described with reference to specific details, it is not intended that such details should be regarded as limitations upon the scope of the invention, except as and to the extent that they are included in the accompanying claims.

What is claimed is:

1. A process for synthesizing 4-amino-2,4-dioxobutanoic acid, comprising:
   reacting diethyl oxalate with an alkoxide in an alcoholic solvent to form a reaction mixture, and afterward
   adding ethyl cyanoacetate to the reaction mixture and allowing a reaction to proceed under conditions suitable to form a first reaction product of the formula diethyl 2-cyano-3-hydroxy-butenedioate,
   isolating said first reaction product of diethyl 2-cyano-3-hydroxy-butenedioate, and
   reacting said first reaction product of diethyl 2-cyano-3-hydroxy-butenedioate with aqueous hydroxide under conditions suitable to form 4-amino-2,4-dioxobutanoic acid.

2. The process of claim 1 wherein said alkoxide is selected from the group consisting of sodium ethoxide, potassium ethoxide, lithium ethoxide, cesium ethoxide and calcium ethoxide.

3. The process of claim 1 wherein said alcoholic solvent is ethanol.

4. A process for synthesizing 4-amino-2,4-dioxobutanoic acid, comprising:
   reacting diethyl oxalate with an alkoxide in a suitable solvent to form a reaction mixture, and afterward
   adding ethyl cyanoacetate to the reaction mixture, and afterward
   extracting the reaction mixture with a suitable organic solvent and water to form an organic layer and an aqueous layer,
   then separating the aqueous layer from the organic layer, then acidifying the aqueous layer and extracting the acidified aqueous layer with additional suitable organic solvent to form a second aqueous layer and a second organic layer, then isolating diethyl-2-cyano-3-hydroxy-butenedioate from the second organic layer, and then reacting the diethyl-2-cyano-3-hydroxy-butenedioate with an aqueous hydroxide under conditions suitable to form 4-amino-2,4-dioxobutanoic acid.

5. The process of claim 4, wherein the suitable organic solvent for extracting the reaction mixture is dichloromethane.

6. The process of claim 4 wherein the first and second organic layers are combined, and the diethyl-2-cyano-3-hydroxy-butenedioate is isolated from the combined organic layers.

7. The process of claim 4 wherein said alkoxide is sodium ethoxide.

8. The process of claim 4 wherein said alkoxide is selected from the group consisting of sodium ethoxide, potassium ethoxide, lithium ethoxide, cesium ethoxide and calcium ethoxide.

9. The process of claim 4 wherein said suitable solvent is ethanol.

10. The process of claim 7 wherein said suitable solvent is ethanol.

\* \* \* \* \*